US010343187B2

(12) United States Patent
Doyle et al.

(10) Patent No.: US 10,343,187 B2
(45) Date of Patent: Jul. 9, 2019

(54) SYSTEM AND METHOD FOR HARMONIC MODULATION OF STANDING WAVEFIELDS FOR SPATIAL FOCUSING, MANIPULATION, AND PATTERNING

(71) Applicant: Utah Valley University, Orem, UT (US)

(72) Inventors: Timothy Edwin Doyle, Orem, UT (US); Blaine Johnson, Lindon, UT (US); Brian Dale Patchett, Spanish Fork, UT (US); Natalie Charlotte Sullivan, Orem, UT (US)

(73) Assignee: Utah Valley University Foundation, Inc., Orem, UT (US)

( * ) Notice: Subject to any disclaimer, the term of this patent is extended or adjusted under 35 U.S.C. 154(b) by 445 days.

(21) Appl. No.: 15/001,120

(22) Filed: Jan. 19, 2016

(65) Prior Publication Data

US 2016/0208213 A1 Jul. 21, 2016

Related U.S. Application Data

(60) Provisional application No. 62/125,474, filed on Jan. 21, 2015.

(51) Int. Cl.
| | | |
|---|---|---|
| *G01N 33/48* | (2006.01) | |
| *G01N 33/50* | (2006.01) | |
| *B06B 1/02* | (2006.01) | |
| *G01N 33/483* | (2006.01) | |
| *G01R 29/08* | (2006.01) | |
| *A61N 5/06* | (2006.01) | |
| *G10K 11/26* | (2006.01) | |
| *A61N 7/00* | (2006.01) | |
| *A61B 5/00* | (2006.01) | |
| *A61B 18/04* | (2006.01) | |
| *A61N 5/02* | (2006.01) | |
| *A61N 5/067* | (2006.01) | |

(52) U.S. Cl.
CPC ............ *B06B 1/0223* (2013.01); *A61N 5/062* (2013.01); *B06B 1/0269* (2013.01); *G01N 33/4833* (2013.01); *G01R 29/0878* (2013.01); *G10K 11/26* (2013.01); *A61B 5/0059* (2013.01); *A61B 18/042* (2013.01); *A61N 5/02* (2013.01); *A61N 5/0622* (2013.01); *A61N 7/00* (2013.01); *A61N 2005/067* (2013.01); *B06B 2201/76* (2013.01)

(58) Field of Classification Search
None
See application file for complete search history.

(56) References Cited

U.S. PATENT DOCUMENTS

| 4,549,435 A * | 10/1985 | Barmatz ................ G10K 15/00 181/0.5 |
|---|---|---|
| 6,246,895 B1 | 6/2001 | Plewes |
| 2010/0139377 A1 | 6/2010 | Huang et al. |
| 2011/0108707 A1* | 5/2011 | Cui ...................... A61B 5/0059 250/208.1 |
| 2012/0141552 A1 | 6/2012 | Dalecki et al. |
| 2012/0280686 A1* | 11/2012 | White ............... G01R 33/56341 324/309 |
| 2014/0011240 A1 | 1/2014 | Lipkens et al. |
| 2015/0165091 A1 | 6/2015 | Dalecki et al. |
| 2015/0210979 A1 | 7/2015 | Wanis |

FOREIGN PATENT DOCUMENTS

WO   WO 2013/182229 A1 * 12/2013

OTHER PUBLICATIONS

Doyle et al. Simulation of elastic wave scattering in cells and tissues at the microscopic level. The Journal of the Acoustical Society of America, vol. 125, pp. 1751-1767. (Year: 2009).*
Lev Ostrovsky, "Concentration of microparticles and bubbles in standing waves", Journal Acoustical Society of America, 138 (6), Dec. 2015, pp. 3607-3612.
Kelley A. Garvin et al., "Controlling collagen fiber microstructure in three-dimensional hydrogels using ultrasound", Journal of Acoustical Society of America, vol. 134, No. 2, Pt 2, Aug. 2013, pp. 1491-1502.
Timothy E Doyle et al., "High-frequency ultrasound for intraoperative margin assessments in breast conservation surgery: a feasibility study", BioMed Central, http://www.biomedcentraol.com/147-2407/11/444, 2011, 15 pages.
Timothy E Doyle et al., "Histology-based simulations for the ultrasonic detection of microscopic cancer in vivo", JASA Express Letters, Journal of Acoustical Society of America, vol. 122, No. 6, Dec. 2007, pp. EL210-EL216.
Timothy E Doyle et al., Modeling the Permittivity of Two-Phase Media Containing Monodisperse Spheres: Effects of Microstructure and Multiple Scattering, Utah State University DigialCommons@USU, The American Physical Society, Aug. 7, 2007, pp. 054203-1-054203-14.
Kai Feng et al., "Numerical analysis of the transportation characteristics of a self-running sliding stage based on near-field acoustic levitation", Journal Acoustical Society of America, 138 (6), Dec. 2015, pp. 3723-3732.

(Continued)

*Primary Examiner* — Russell S Negin
(74) *Attorney, Agent, or Firm* — Kunzler Bean & Adamson

(57) ABSTRACT

An system, and method are disclosed for harmonic modulation of standing wavefields for spatial focusing, manipulation, and patterning of particles, cells, powders, aerosols, colloids, and solids using a multifrequency wave source, a chamber a control module and an analysis module to generate standard wavefields useful for tissue engineering, micro fabrication, therapeutic treatment, and diagnostic tests.

15 Claims, 17 Drawing Sheets

(56) References Cited

OTHER PUBLICATIONS

Carrie Poppy, Physicists Use Souond to Levitate Cells and Check for Cancer, Tech Times, http://www.techtimes.com/articles/104948/20151110/physicists-use-sound-levitate-cells-check-cancer.htm, Nov. 10, 2015.
"Sound Waves Levitate Cells (acoustic levitation) to Detect Stiffness Changes That Could Signal Disease", Innovation Toronto, http://www.innovationtoronto.com/2015/11/sound-waves-levitate-cells-acoustic-levitation-to-detect-stiffness-changes-that-could-signal-disease/, Nov. 6, 2015.
"Sound Waves Levitate Cells to Detect Stiffness Changes That Could Signal Disease", Wise, www.newswise.com/articles/sound-waves-levitate-cells-to-detect-stiffness-changes-that-could-signal-disease, Nov. 4, 2015.
"Sound Waves Levitate Cells to Detect Stiffness Changes That Could Signal Disease", Phys.Org, http://phys.org/print36586342.html, Nov. 4, 2015.
"Sound Waves Levitate Cells to Detect Stiffness Changes That Could Signal Disease", ScienceDaily, https://www.sciencedaily.com/releases/2015/11/151104151012.htm, Nov. 4, 2015.
Kelley A. Garvin et al., "Spatial patterning of endothelial cells and vascular network formation using ultrasound standing wave fields", Journal of Acoustical Society of America, vol. 134, No. 2, Pt 2, Aug. 2013, pp. 1483-1490.
Ernest L. Madsen et al., "Tissue mimicking materials for ultrsound phantoms", Medical Physics, vol. 5, No. 5, Oct. 1978, pp. 391-394.
PCT/US16/13967, Notification of Transmittal of the International Search Report and the Written Opinion of the International Searching Authority, or the Declaration, dated May 20, 2016.

\* cited by examiner

1200

SYSTEM AND METHOD FOR HARMONIC MODULATION OF STANDING WAVEFIELDS FOR SPATIAL FOCUSING, MANIPULATION, AND PATTERNING

CROSS-REFERENCES TO RELATED APPLICATIONS

This application claims priority under 35 U.S.C. § 119(e) to U.S. to Provisional Application No. 62/125,474, entitled "Harmonic Modulation of Standing Wavefields for Spatial Focusing and Patterning" and filed on Jan. 19, 2015 for Timothy Edwin Doyle, which is incorporated herein by reference.

FIELD OF THE INVENTION

This invention relates to levitation by means of standing wave fields and more particularly relates to structured levitation using multiple harmonic standing wave fields.

BACKGROUND

Description of the Related Art

A significant problem in tissue engineering and regeneration is facilitating the growth of artificial tissues with complex biological structures. Cells often grow in random close-packed structures in two-dimensional (2D) and three-dimensional (3D) tissue cultures. Natural biological structures, however, are typically comprised of cells that are arranged in convoluted layers, surfaces, tubules, ducts, lobules, and cavities. Examples of such structures include pulmonary alveoli and renal corpuscles. Creating artificial tissues with such complex structures in three dimensions, and that are additionally functional in the human body, is currently one of the biggest challenges in tissue engineering. Tissue templates are therefore used to guide cells into forming complex tissue microstructures.

To date, most templates for tissue engineering have comprised either 2D surfaces or 3D scaffolds to provide a substrate for cell growth. These templates include both artificial materials, such as polymer meshes, and natural materials, such as the extracellular matrix of tissues from animals or human donors from which the cells have been removed. The problems with these methods include the biocompatibility of the substrate material; the geometric limitations of 2D surfaces or 3D scaffolds; the functionality of the artificial tissue if the scaffold or surface is permanent; biochemical and biomechanical issues arising from degradable or bio-absorbable substrates; and the potential for microbial biofilm growth on the surface or scaffold.

Acoustic forces have been used in various forms over the past few decades to manipulate living cells. Acoustic tweezers have been proposed and demonstrated for the manipulation of single cells in microscopy and biological research. Standing-wave acoustic traps have also been developed for similar applications, and the aggregation of cells suspended in a fluid has been demonstrated for very simple standing-wave patterns. Microfluidic devices that use acoustic standing waves have been investigated for medical applications such as separating erythrocytes, platelets, or lipid particles in blood. The concentration of living biological cells (erythrocytes) with standing-wave acoustic fields has been demonstrated for extended periods of time (>15 minutes) without damage to the cells, indicating the potential of this technology for more extensive biomedical applications. Acoustic forces and piezoelectric devices have also been applied to develop a tissue engineering approach that uses inkjet technology. This approach sprays cells onto a substrate in complex patterns to create artificial tissues. However, since the approach still requires a substrate and deposits a 2D layer of cells with each scan, it suffers from many of the same disadvantages as those employing 2D surfaces and 3D templates.

Acoustic standing waves are an active area in biomedical research, particularly in biosensing applications and microfluidic devices. Basic standing-wave patterns have been used to engineer tissues and biomaterials with simple planar geometries. However, the use of acoustic fields to generate a complex nonmaterial or virtual template for tissue engineering has not been previously achieved due to the complexity of the wave field pattern that would have to be created in the culture medium.

To date, acoustic and electromagnetic waves have been spatially focused by the following methods: 1.) Having the surface of the transmitting element constructed into a specific shape, such as an acoustic transducer fabricated with a concave face to focus the acoustic wave to a point; 2.) Incorporating elements that refract or reflect the waves, such as lenses or mirrors, to focus the waves into a desired location or pattern; 3.) Using multiple transmitting sources at different positions to generate interference patterns that create wavefields of a desired pattern; and 4.) Using multiple transmitting sources as an array, and altering the phases of the waves transmitted from each source to create a wavefield with a steerable focus, as in phased array imaging. A need exists for more precise and effective focusing of electromagnetic waves using a more convenient, less cumbersome method.

SUMMARY

From the foregoing discussion, it should be apparent that a need exists for a system and method that effectively and efficiently focus electromagnetic and/or acoustical waves to generate a complex nonmaterial or virtual template for tissue engineering and other applications. Beneficially, such a system and method would accommodate particulate, cellular, solid and other materials and would be programmable for a variety of structures and would function without mandatory changes to the physical configuration of the wave source.

The present invention has been developed in response to the present state of the art, and in particular, in response to the problems and needs in the art that have not yet been fully solved by currently available tissue engineering and micro-manipulation and patterning techniques. Accordingly, the present invention has been developed to provide a system and method for creating non-material or virtual templates that overcome many or all of the above-discussed shortcomings in the art.

Herein provided is a system for spatially focusing and patterning a standing wavefield. In certain embodiments the system comprises at least one multifrequency wave source, a chamber configured to generate a standing wavefield, a control module to modulate the amplitudes of individual harmonics in order to generate a desired standing wavefield pattern, and an analysis module to calculate the amplitudes of individual harmonics corresponding to a desired standing wavefield pattern, material structure, or material configuration.

In some embodiments the shape of the chamber is configured to generate a standing wavefield comprising cubical, cylindrical, spherical, spheroid, conical, polyhedral, prismatic, rhombohedral, or other geometry. The multifrequency wave source may comprise a wave transmitter, a wave transducer, an acoustic transducer, an electromagnetic antenna, a laser harmonic frequency generator, and/or maser harmonic frequency generator. The multifrequency wave source sometimes comprises a miniaturized, multicomponent radio-frequency (RF) generator, a microwave antenna with harmonic frequency capability, and/or an acoustic filter comprising an acoustical metamaterial. In some embodiments the multifrequency wave source comprises a Sound Amplification by Stimulated Emission of Radiation (SASER) in combination with nonlinear higher-order harmonic generation and/or harmonic generation from the acoustic scattering of single-frequency plane waves from small orifices, and/or a tunable, narrow-band filter in combination with a broadband electromagnetic or optical source.

The wave transducer sometimes comprises a piezoelectric transducer comprising stacked piezoelectric elements electrically isolated from each other. A first stacked piezoelectric element may be of different thicknesses than a second stacked piezoelectric element and may be configured to tune that element to a unique harmonic frequency. In certain embodiments the stacked piezoelectric elements are driven in concert by a voltage source to produce multifrequency wave fields. In some embodiments the acoustic transducer comprises a broadband acoustic transducer driven by an arbitrary waveform generator to directly produce a specified standing wave pattern.

A method of the present invention is also presented for spatially focusing and patterning a standing wavefield. The method in the disclosed embodiments substantially includes the steps necessary to carry out the functions presented above with respect to the operation of the described system. In one embodiment, the method includes providing at least one multifrequency wave source, providing at least one chamber structured to generate standing a wavefield, providing at least one control module to modulate the amplitudes of individual harmonics in order to generate a desired standing wavefield pattern, identifying at least one desired standing wavefield pattern, generating at least one standing wave according to the desired standing wavefield pattern, generating at least one harmonic standing wave according to the desired standing wavefield pattern, comparing the resulting combined multifrequency standing wavefield to the desired wavefield pattern, adjusting the standing waves if necessary and fine tuning the multifrequency standing wavefield as necessary;

In some embodiments the wavefields comprise acoustic waves in fluids, stress-strain fields corresponding to acoustic waves in solids, electromagnetic fields, particle density fields (e.g., ions or electrons in a plasma, metal, or ionic conductor), and the like. The method herein sometimes comprises generating stable nodal regions for electromagnetic, and optical levitation and manipulation. The sable nodal regions may facilitate fabrication of solid material, fluid material, and/or particulate matter in suspension. The particulate matter in suspension may comprise biological cells, non-biological material, a colloid, an aerosol and/or a powder.

The desired wavefield pattern sometimes generates an antinodal region with highly-localized, high acoustic pressures configured to produce enhanced cavitation, sonoluminescence, sonochemistry in fluids, tissue ablation in tissue engineering or cancer therapy, ultrasonic stimulation of neurons in vivo, and/or the initiating of at least one of physical, chemical, and biological processes. In various embodiments the desired wavefield pattern generates an antinodal region with highly-localized, high electromagnetic field strengths that can be used to produce electromagnetic stimulation of neurons in vivo, localized optical focusing for ultra-resolution optical microscopy, RF or microwave focusing for heating or sensing applications, electromagnetic focusing for the control of ionized plasmas, and/or the initiating of at least one of physical, chemical, and biological processes.

The desired wavefield pattern of the method herein sometimes generates an antinodal region with highly-localized, high acoustic pressures configured to create a well-defined channel and/or a well defined cavity in biological or non-biological materials. In some embodiments the method provided herein comprises the patterning of cells into realistic tissue structures for tissue engineering. In various embodiments the method comprises the patterning, consolidation, and bonding of particles for the fabrication of parts and devices having complex shapes, and/or the stabilization of cell or particle layers in acoustic standing wave chambers or channels for nondestructive testing via ultrasonic, optical, or other noninvasive means. The method sometimes comprises the refined separation of cells or particles for medical, chemical, or industrial processes, and microfluidic control of cells or particles without the need for conventional microfluidic devices with fixed channels and chambers.

The method herein may comprise computational modeling of the wavefield using Fourier analysis, wavelet analysis, and/or other waveform analysis methods to focus the nodal or antinodal regions in a standing wave, generate complex node-antinode patterns in the standing wave, and/or to select a set of frequencies and source locations to produce specified particle structures. Some embodiments comprise providing plurality of acoustical sources with the capability of generating acoustic waves comprised of a plurality of distinct frequencies to form standing waves that superimpose (sum), creating a complex standing wavefield structure with stable, highly defined nodal surfaces that function as a virtual template for holding particles in complex, highly stable, and highly resolved patterns. The standing wavefield structure may comprise a pattern in one, two, or three dimensions having a planar, cylindrical, spherical, spheroidal or other geometry. In certain embodiments the standing wavefield stucture generates complex combinations of nodal surfaces forming at least one of double-wall features, triple-wall features, other multiple wall features and other geometric configurations of nodal surfaces.

Further provided herein is a method for cellular or tissue modeling using harmonic modulation of standing wavefields for spatial focusing and patterning. The method in the disclosed embodiments substantially includes the steps necessary to carry out the functions presented above with respect to the operation of the described system. In one embodiment, the method includes the steps: select a target tissue, analyze the structure of the target tissue, model a standing wavefield that mimics that structure of the target tissue, program at least one multifrequency wave transmitter to generate the waves necessary to create the standing wavefield, provide a chamber configured to create a standing wavefield, provide a suitable medium within the chamber, add the selected cells to the medium, generate the waves necessary to create the standing wavefield, apply the waves to the chamber, and allow sufficient time for the cells to organize into the form dictated by the standing wavefield. In some embodiments the method further comprises repeating the steps for complex tissues to pattern other cell types.

In certain embodiments a plurality of multifrequency wave sources are positioned at least one of 90°, and 120° relative to each other in order to create templates for periodic three-dimensional channels with square, rectangular, triangular, or rhombohedral symmetry. Some embodiments comprise a plurality of acoustic sources with five-fold (108°), seven-fold (128.57°), and eight-fold (135°) symmetry creating standing waves as templates for aperiodic and random cell structures resembling tissue microstructures and/or disordered or quasi-crystalline patterns in atomic structures. The multifrequency wave sources are sometimes positioned at other angles relative to each other.

The chamber sometimes comprises cylindrical, conical, cubic, polyhedral, spherical, spheroid, rhombohedral, prismatic, or other geometry. The method herein sometimes generates an acoustic standing wavefield as a force field to confine the cells or particles to virtual channels and/or chambers through which they flow. A microstructure of the target tissue may be analyzed with 3D Fourier analysis by microtoming and imaging successive slices of a tissue sample, 3D microscopic computed tomography (micro-CT), and/or other 3D image reconstruction methods.

In certain embodiments the standing wave generated comprises amplitude spikes corresponding to antinodal regions in which tissue structures with continuous channels (ducts, capillaries, bronchioles) and cavities (alveoli) could form, and nodal regions in which tissue structures such as regular cell clusters (lobules) and sheets (tissue layers, linings, walls, and membranes) could form.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description numerous specific details are provided to facilitate a thorough understanding of embodiments of the invention. One skilled in the relevant art will recognize, however, that the invention may be practiced without one or more of the specific details or with other methods, components, materials, and so forth. In other instances well-known structures, materials, or operations are not shown or described in detail to avoid obscuring aspects of the invention.

The schematic method diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1A:
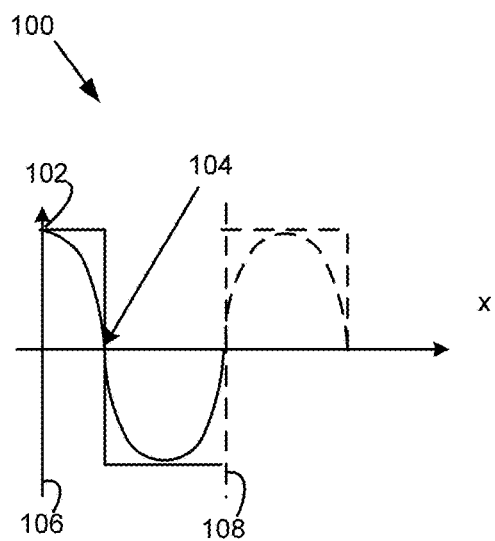
FIGS. 1A-1C depicts examples of standing wave patterns than can be generated using harmonic modulation or synthesis in accordance with the present invention.
Figure 1B:
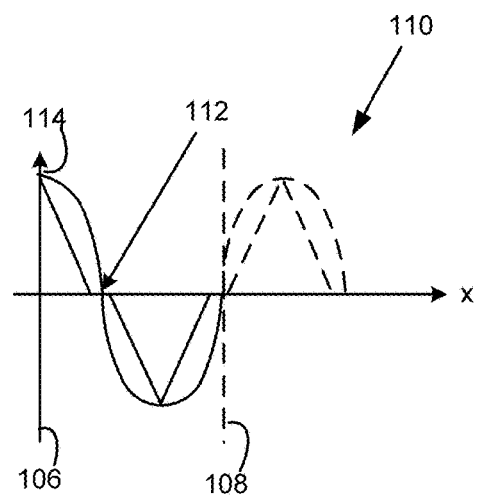
Figure 1C:
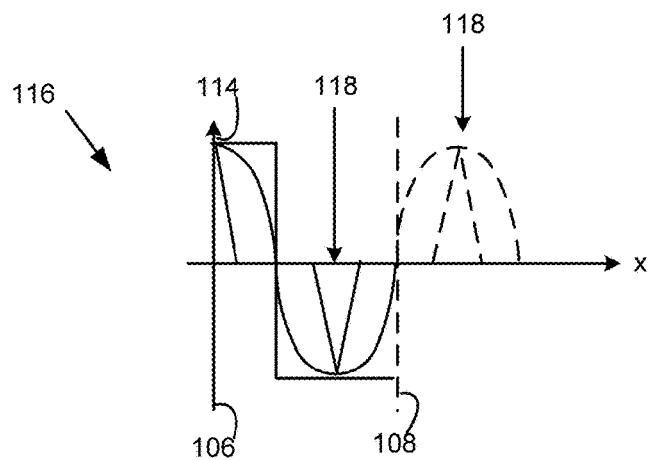

FIGS. 1A-1C displays examples of standing wave patterns than can be generated using harmonic modulation or synthesis. As illustrated an acoustic wave 100 and its pressure field 102 are generated by a transducer 106, transmitted through a fluid (not shown), and reflected from a hard surface, or reflector 108. FIG. 1A displays the classic example of the square wave pattern. In this example, the node or particle levitation region 104 is unstable because of the large gradient in the pressure field at the node. 1a diagrams a transducer (unclamped end) 106, an increasing pressure gradient 102, an unstable levitation region 104, and a reflector (clamped end) 108. The pressure field (curved line) is generated from an acoustic standing wave in a cavity, with harmonic modulation to produce an ideal square wave, which produces an unstable nodal or levitation region by creating a steep pressure gradient. FIG. 1B illustrates an embodiment of harmonic modulation to produce a modified sawtooth wave 110, which produces a stable nodal or levitation region 112 with a flat pressure gradient 114. The flat regions 112 at the nodes of the sawtooth wave 110 stabilize the levitation region since particles (not shown) would not experience a pressure gradient 102 in these regions. FIG. 1c illustrates an embodiment of harmonic modulation to produce an ideal spike wave 116, which localizes the wavefield pressure 114. Sharp pressure spikes 118 may occur at the antinode positions. An embodiment of optimal levitation condition may comprise a pressure "well", which could tightly confine the particles between two adjacent pressure spikes 118. FIGS. 1B and 1C illustrate embodiments of theoretical wavefields that would require a very large number of harmonic modes ranging to very high frequencies to produce. In practice, only a small number of harmonic modes would be necessary to produce a good approximation to an example such as the square wave in FIG. 1A.

Figure 2A:
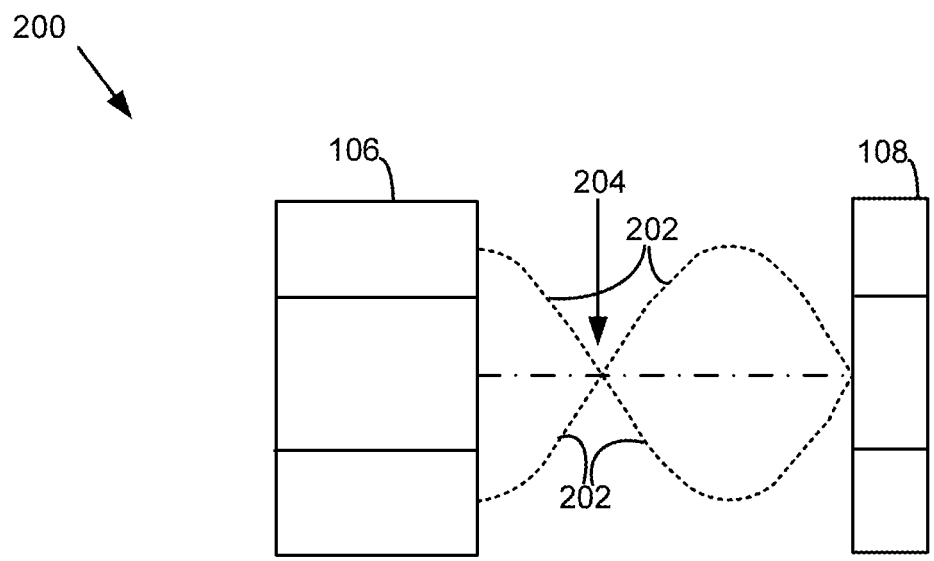
FIGS. 2A-2D depicts an embodiment of harmonic modulation of a fundamental standing wave mode 2A with two 2B, four 2C, and seven 2D harmonic modes to produce an approximation of a square wave in accordance with the present invention.
Figure 2B:
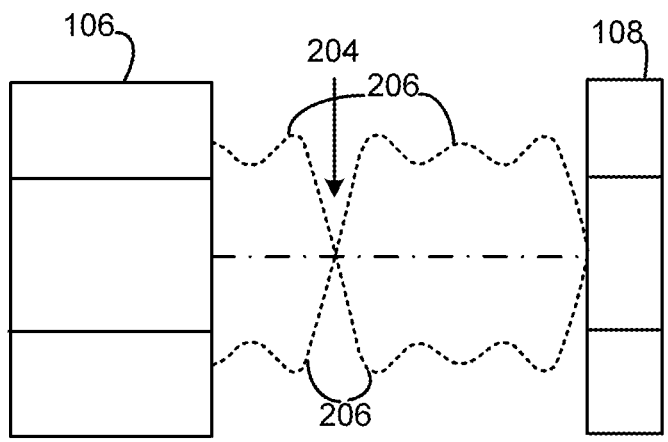
Figure 2C:
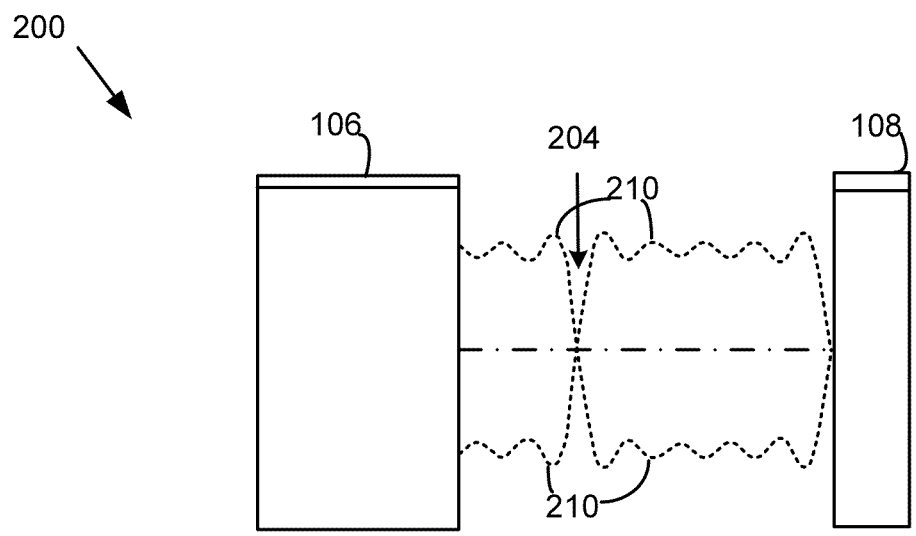
Figure 2D:
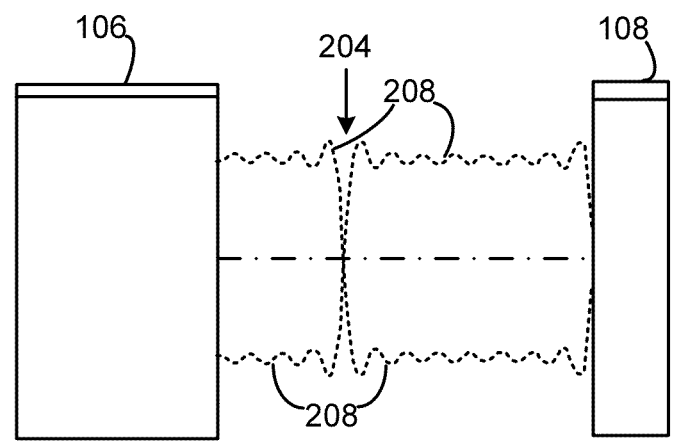

FIGS. 2A-2D illustrates an embodiment of the harmonic modulation 200 of a fundamental wave mode, FIG. 2A, in accordance with the present invention. As illustrated FIG. 2B uses two, FIG. 2C uses four, and FIG. 2D uses seven harmonic modes to produce an approximations 206, 208, an 210 of a square wave. The illustrated embodiment depicts a transducer 106, a standing wave 202, a nodal 204 region forming a levitation point and a reflector 108 for each modulation.

Acoustic standing waves may be generated in a confined fluid. For example, if an acoustic source is placed against one face of a cubic chamber filled with fluid, longitudinal standing waves will be generated in the fluid at frequencies which are inversely proportional to the size of the cube. If the acoustic source is emitting a single frequency, then the pressure field of the standing wave 202 may be described with a cosine wave, and the nodal 204 regions may be described as planar surfaces parallel to the cube faces. Cells or particles may collect at the nodal 204 regions since the acoustic forces and pressures are zero there. However, in some cases the nodal 204 regions are not well defined since the acoustic pressure gradually increases away from the nodal 204 surface due to the pure cosine function. Cells and particles with motion may therefore oscillate about the nodal 204 surface, thus creating an ill-defined nodal region 204.

Acoustic waves of multiple frequencies may be used, however, to more sharply define the nodal 204 region and resulting particle structure. For example, higher-order harmonic waves may be used to modify the shape of the standing wave 202 to more tightly confine the cells and particles in the nodal 204 region. In some embodiments, the cosine waveform of the standing wave 202 may be modified with harmonics to resemble a square wave 100, a modified sawtooth wave 110, or a double spike structure 116 with a pressure well at the nodal 204 points. Such a wave modifications may be used to create a much more narrow and well-defined nodal 204 region where the acoustic pressure steeply increases away from the nodal 204 (zero acoustic pressure) surface and simultaneously tightly binds the cells or particles by creating a potential well with respect to the pressure. Cells and particles with motion may therefore be more tightly restricted to the nodal 204 surface, thus creating a well-defined nodal 204 region. The increased definition of the nodal 204 region may also increase its stability with respect to particle motion and the shape of the composite particle structure. For example, particles in a planar nodal 204 surface may oscillate in and out of the nodal 204 region less frequently, and the nodal 204 surface may maintain a more well-defined planar geometry.

Various embodiments of the technology provided herein employ acoustic or electromagnetic sources that can generate multiple, distinct frequencies. A piezoelectric transducer may have stacked piezoelectric elements. The transducers sometimes comprise piezoelectric elements of different thicknesses stacked on top of each other and, in some embodiments, electrically isolated from each other to facilitate independent electrical excitation of that element's specific frequency. The different thickness of each element may tune the element to a different harmonic frequency. When driven in concert by a voltage source, the combination of elements may produce multifrequency wave fields more similar in structure to the ideal wave fields used in the computer simulations illustrated in FIGS. 3, 6, 7, 8, 9, and 10 herein. A broadband acoustic transducer may be driven by an arbitrary waveform generator to directly produce the desired standing wave pattern. In some embodiments a broadband piezoelectric transducer used in combination with one or more narrow-band acoustic filters. The broadband transducer may be pulsed at a high pulse repetition frequency. The acoustic filters are sometimes made from acoustic metamaterials. In certain embodiments a SASER (Sound Amplification by Stimulated Emission of Radiation) is used in combination with nonlinear higher-order harmonic generation. Some embodiments employ harmonic generation from the acoustic scattering of single-frequency plane waves from small orifices. Various embodiments use new acoustic metamaterials that exhibit phenomena analogous to frequency mixing processes in nonlinear optics.

Various embodiments multifrequency electromagnetic sources comprise harmonic frequency generation in lasers, harmonic frequency generation in masers, miniaturized, multicomponent radio-frequency (RF) and microwave antennas with harmonic frequency capability, and the use of metamaterials as tunable narrow-band filters in combination with a broadband electromagnetic or optical source.

Figure 3A:
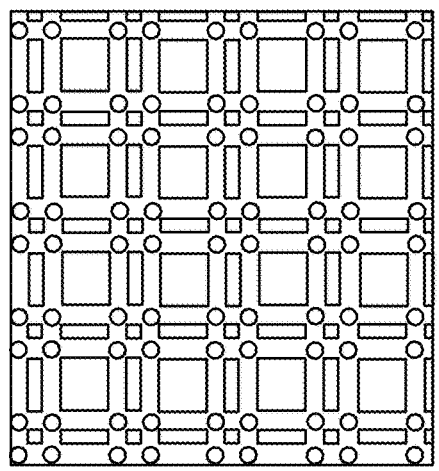
FIGS. 3A-3C depicts embodiments of computer simulations of periodic three-dimensional channels created with square 3A, rectangular 3B, and hexagonal 3C symmetries using harmonic modulation and placement of two acoustic sources at 90° 3A-B and 120° 3C orientations with respect to each other in accordance with an embodiment of the present invention.
Figure 3B:
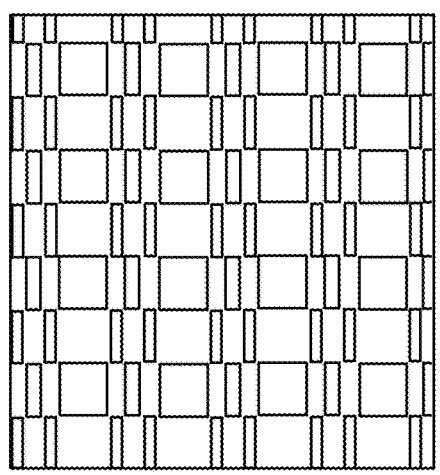
Figure 3C:
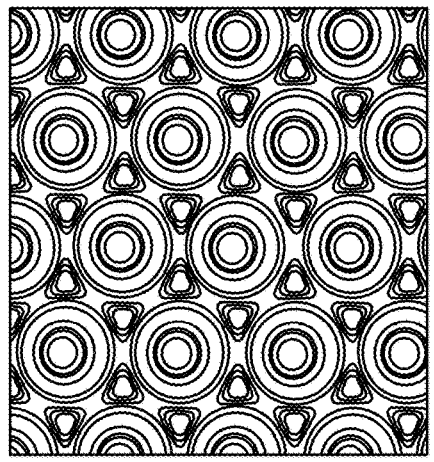

FIGS. 3A-3C depict embodiments 300 of computer simulations of periodic three-dimensional channels created with square 3A, rectangular 3B, and hexagonal 3C symmetries using harmonic modulation and placement of two acoustic sources at 90° 3A-B, and 120° 3C orientations with respect to each other in accordance with the present invention. The harmonic modulations create well-defined, multilayered channel walls, or interlaced channel structures with different channel sizes.

The use of multiple sources and multiple frequencies for the acoustic waves, standing waves may be generated with a wide range of complex structures. In various embodiments, periodic three-dimensional channels may be created with square, rectangular, triangular, and rhombohedral symmetries using placement of acoustic sources at 90° and 120° orientations with respect to each other. Aperiodic structures may be created using placement of acoustic sources with five-fold (108°), seven-fold (128.57°), and eight-fold (135°) symmetries. Since such symmetries cannot tile two- and three-dimensional spaces, resulting cell structures from such standing waves could be aperiodic and random, much like many tissue microstructures. In atomic structures, five- and seven-fold symmetries are incommensurate and form disordered or quasi-crystalline patterns. Other positioning is sometimes employed to created other specialized patterns or structures.

In certain embodiments complex structures are generated in a cell or particle suspension in a cylindrical chamber. The resulting standing waves may be described by cylindrical wave functions, and excitation of different standing wave modes could be used to create structures with axial channels clustered around the chamber's axis and cuboidal chambers encircling the channels. Such composite cell structures could be used to engineer lobular-type tissue microstructures such as those found in the lung (alveoli) or kidney (glomeruli).

Dendritic alveolar structures may be patterned using a conical confinement chamber and multiple frequencies. The standing waves may be the resonant modes of a cone, and could have conical symmetry, might follow a conical coordinate system, and be modeled and represented with conical wave functions.

In some embodiments microfluidic control of cells or particles is achieved without the need for conventional microfluidic devices with fixed channels and chambers. Acoustic standing wavefields may be used as a force field to confine the cells or particles to virtual channels and chambers through which they would flow. In various embodiments an acoustic wavefield structure is modified by modifying its frequency content, source positions, and phase. Thus, the virtual microfluidic device may be rapidly reconfigured to perform many different functions.

Certain embodiments focus the antinodal regions of standing waves into spikes. Such embodiments comprise acoustic cavitation in fluids, sonochemistry, sonoluminescence, tissue ablation in tissue engineering or cancer therapy, ultrasonic and electromagnetic stimulation of neurons in vivo. localized optical focusing for ultra-resolution optical microscopy, and RF or microwave focusing for heating or sensing applications.

Figure 4A:
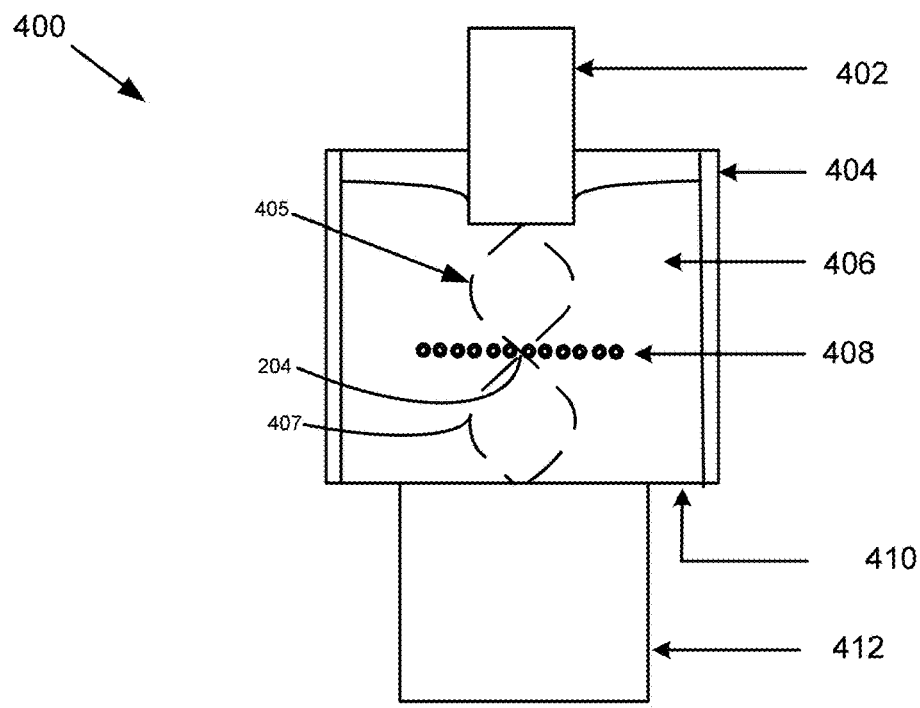
FIGS. 4A-4B depicts an embodiment of a device using acoustic levitation to produce a layer of cells suspended in a liquid medium in accordance with the present invention.
Figure 4B:
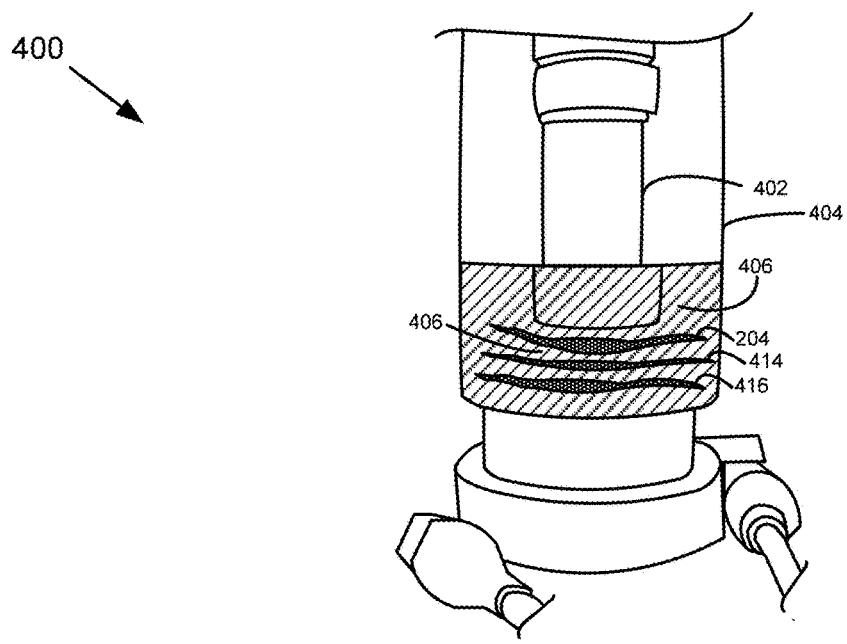

FIGS. 4A-4B depict an embodiment of a device 400 using acoustic levitation to produce a layer of cells 408 suspended in a liquid medium 406 in accordance with the present invention. FIG. 4A is a schematic line drawing depicting an embodiment of the device 400 comprising a 50 MHz-prove transducer 402, a cylindrical well 404, fluid 406, a standing wave 405, a node 204, an antinode 407, a cell layer 408, a thin plastic film 410, and a 200 kHz levitation transducer 412. FIG. 4B is line drawing of a photographic depiction of the device 400 demonstrating acoustic levitation of cell-mimicking buoyancy neutral microspheres 414 in water 406 in a cylindrical well 404 using an upper transducer 402 and a lower transducer 412. The microspheres 414 form layers 416 at the standing-wave nodes. Such layers 416 are necessary for probing with HF ultrasound and acquiring a coherent pulse reflection. In some embodiments the cell layer 416 can then be probed with HF ultrasound to obtain cell biomechanical properties without interfering reflections and adhesion forces due to the culture plate.

The use of acoustic standing waves for the purpose of tissue engineering relies on the phenomenon of acoustic levitation. In acoustic levitation, a standing wave 405 is generated in a closed cavity 404 or acoustic region with the use of ultrasound tuned to a specific frequency conducive to forming the standing wave 405. Such a standing wave 405 has nodes 204 where the wave pressure does not vary and antinodes 407 where the wave pressure shows the greatest variation. Particles 414 in the fluid (air or liquid) 406 are forced away from the antinodes 407 due to the changing pressure, accumulate at the nodal regions, 204 and form layers. FIG. 4 illustrates acoustic levitation to suspend microparticles 414 and cells 408 in a fluid 406 for testing with high-frequency (50 MHz) ultrasound.

When applied to tissue engineering, cells 408 in a growth medium 406 (fluid or gel) are exposed to acoustic standing waves 405. The cells 408 accumulate at the nodal regions 204, where they continue to reproduce as well as release proteins and other biomolecules to adhere to each other and produce an extracellular matrix. The cell 406 layers 416 are thus organized into forming a layered tissue structure. A standing wave 405 comprised of multiple frequencies facilitates this process. To maintain the characteristics of a standing wave 405, the frequencies may be harmonics of the fundamental or lowest standing-wave frequency. The interference pattern created by the multiple frequencies enables the modulation of the standing wave and the custom tailoring of its properties. For example, in FIG. 4B, the transducer 402, 412 is being driven by a square-wave voltage pattern, which is forcing the transducer 402, 412 to produce wave frequencies of the fundamental and first four odd harmonics. This combination of frequencies produces a nodal region 204 that is much more focused (thinner and highly defined) as illustrated in 4B than that produced by the simple sine wave shown in 4A. Since the pressure gradients near the node 204 are greater in 4B than in 4A, the levitated microparticles 414 or cells 408 form a much more stable and defined layer 416.

Figure 5A:
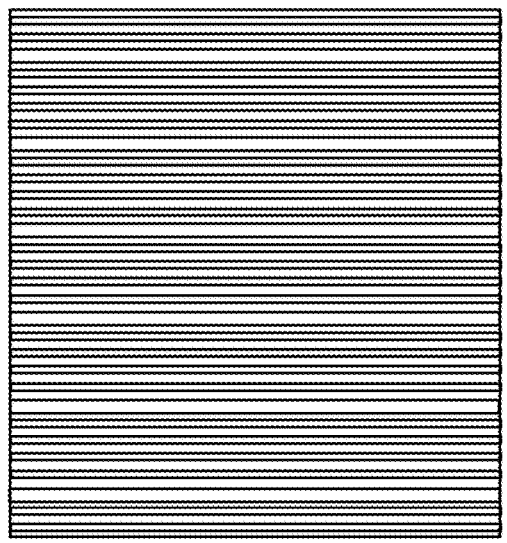
FIGS. 5A-5C depicts a computer model of ultrasonic standing wave-field patterns and nodes in accordance with an embodiment of the present invention.
Figure 5B:
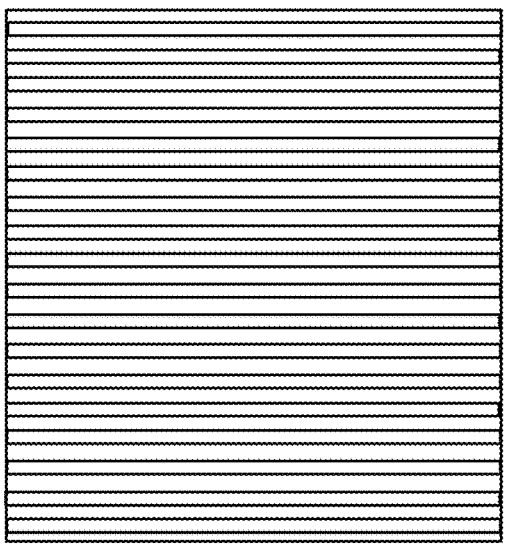
Figure 5C:
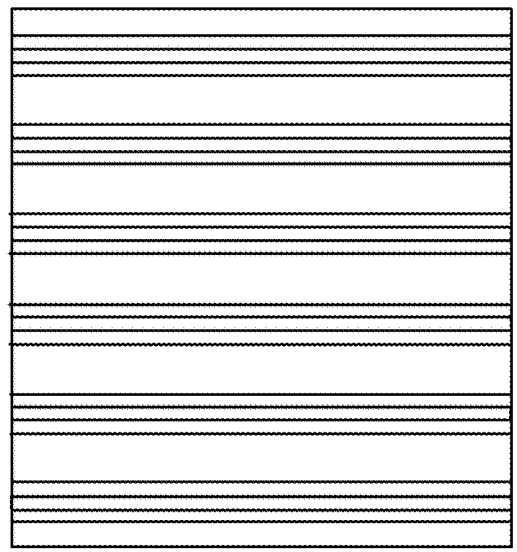

FIGS. 5A-5C depict an embodiment of computer model 500 of the nodal focusing effect for an ultrasonic standing wave-field in accordance with the present invention. The illustrated embodiment shows the nodal focusing effect with six nodes illustrating the nodes as dark lines for a single-frequency sine wave 5A, a square wave generated from three frequencies (fundamental and first two odd harmonics) 5B, and a square wave generated from five frequencies (fundamental and first four odd harmonics) 5C. The model displays the absolute values of the pressure fields and nodes for a simple sine wave driving the transducer with a single frequency 5A, a square wave driving the transducer to emit three ultrasonic frequencies 5B, and a square wave driving the transducer to emit five ultrasonic frequencies 5C. As illustrated the nodal regions grow thinner and more defined with the accumulation of additional frequencies, with greater sharpness and definition of the nodes in 5B and 5C as compared to 5A. Other nodal patterns may be generated as well by altering the amplitudes of the harmonic frequencies. Such patterns could include double or triple thin nodal layers, or thick nodal layers separated by thin antinodal regions.

Figure 6A:
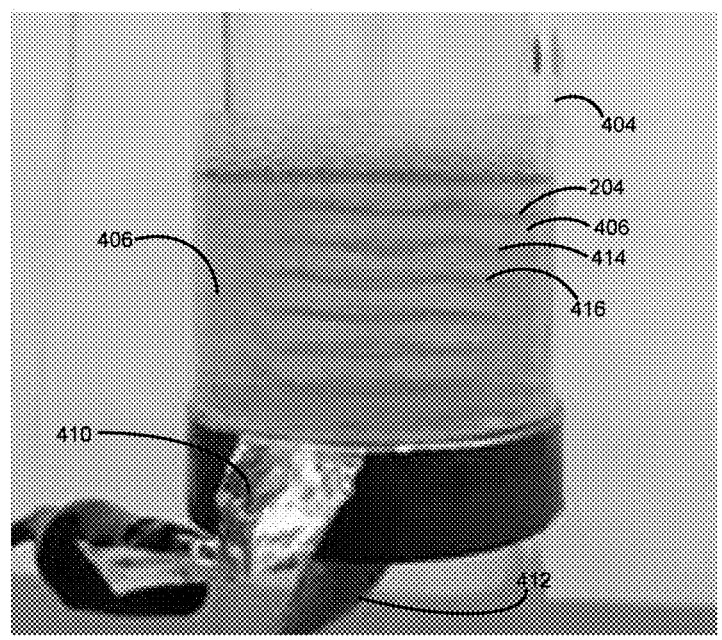
FIGS. 6A-6B depicts an experimental demonstration of an embodiment of node focusing with the use of multiple harmonic frequencies using cell-mimicking buoyancy neutral microspheres in water in accordance with the present invention.
Figure 6B:
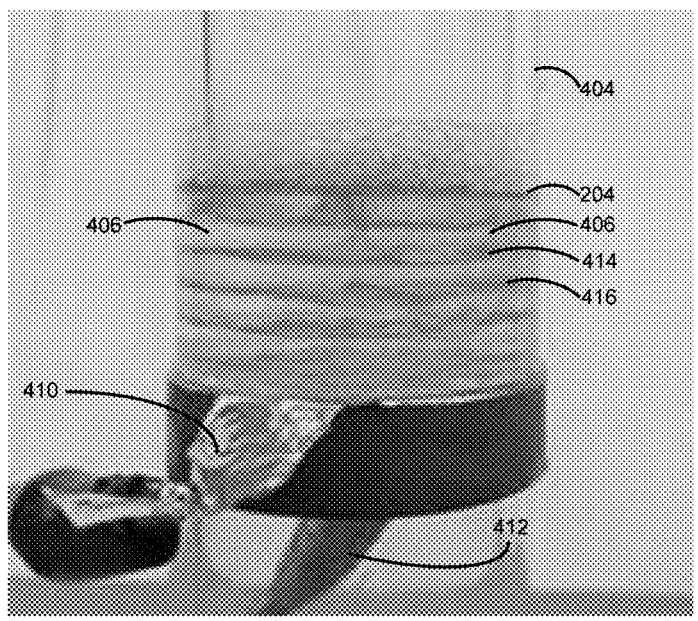

FIGS. 6A-6B depict embodiments of experimental verification 600 of the use of harmonic frequencies to modulate the standing wave and focus the nodal regions using cell-mimicking buoyancy neutral microspheres 414 in water 406 in accordance with the present invention. For FIG. 6A an ultrasonic transducer was driven by a sine-wave voltage source (single frequency). FIG. 6B used an ultrasonic transducer driven by a square-wave voltage source (fundamental frequency and odd harmonics) thus producing greater sharpness and definition of the cell layers in 6B as compared to 6A.

Buoyancy-neutral polyethylene microspheres 414 were suspended in water 406 contained in an acrylic cylinder 404 with a thin sheet of plastic 410 glued to the bottom. A 200-kHz transducer 412 was placed below the cylinder and acoustically coupled to the plastic bottom with ultrasonic gel. In FIG. 6A, a pure sine-wave voltage was applied to the transducer 412, producing a single-frequency standing wave. As predicted by the model shown in FIG. 5A, the microspheres 414 formed thick layers 416 at the nodes, with many microspheres 414 left in suspension between the nodes 204. In FIG. 6B, a square-wave voltage was applied to the transducer, producing higher harmonic frequencies. As predicted by the models shown in FIGS. 5B and 5C, the microspheres 414 formed thinner layers at the nodes 204, with much fewer microspheres 414 between the nodes 204.

In addition to forming thinner, more highly defined layers 416, experiment 6B using a square-wave voltage source produced the layers 416 more rapidly than experiment 6A using the sine-wave voltage source. The layers 416 in 6B were additionally more stable and persisted longer in solution. The results from the computer modeling of FIG. 5 and the experiments here demonstrate that one-dimensional interference patterns created by standing waves of different frequencies can be used to fine-tune and improve the acoustic levitation process. The process of forming these interference patterns is also known as Fourier synthesis, the ability to create any arbitrary waveform from a combination of a set of sine waves of different frequencies.

For example, tissue microstructures from a laboratory animal such as a mouse are analyzed with 3D Fourier analysis. The 3D microstructure of a region of tissue, such as the alveolar structure of lung, are obtained by microtoming and imaging successive slices of a sample of tissue. The image slices are then stacked by a computer program and reconstructed into a 3D representation of the tissue microstructure. Finally, 3D Fourier analysis is performed on the 3D image to obtain the principal spatial frequencies and their amplitudes. The ultrasonic interference patterns may be extended from one dimension to two and three dimensions as well, forming complex patterns that may be used for engineering tissues with microstructures mimicking those found in the human body.

Figure 7A:
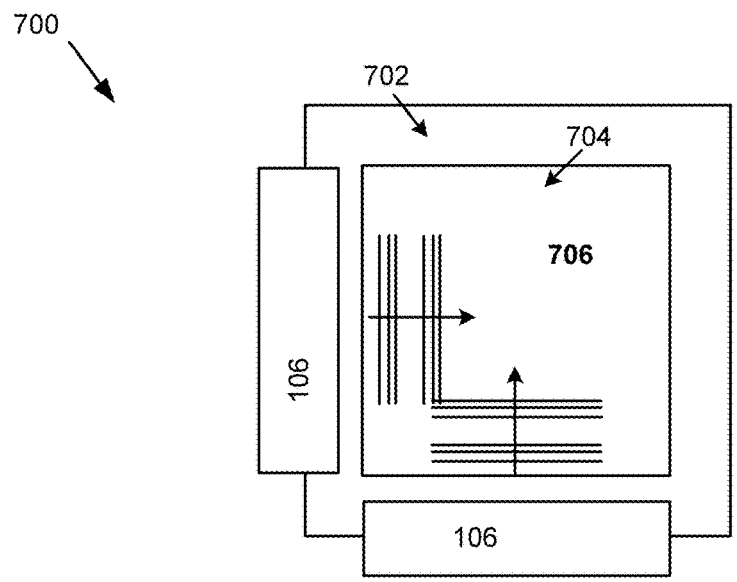
FIGS. 7A-7C depicts an embodiment of the generation of complex 3D node pattern (black lines) using a combination of multiple sources (two transducers), multiple frequencies, and the resulting interference patterns in accordance with the present invention.
Figure 7B:
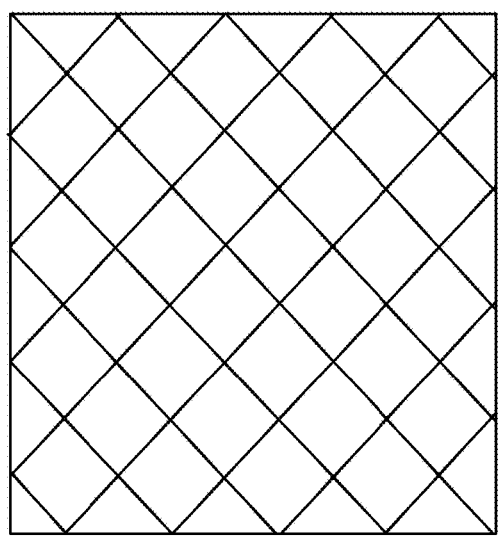
Figure 7C:
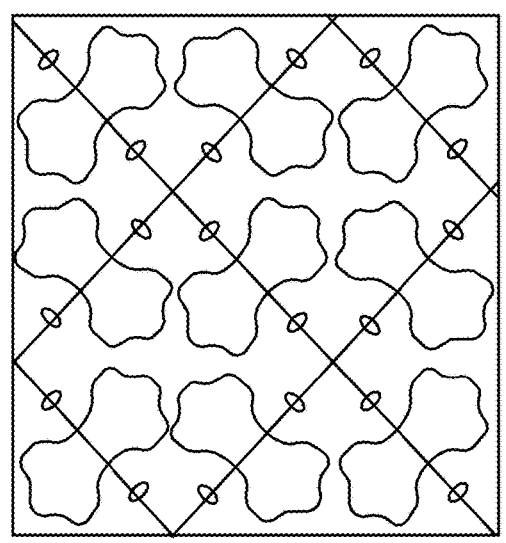

FIGS. 7A-7C depict embodiments of the generation 700 of complex 3D node patterns (black lines) using a combination of two transducers 106, multiple frequencies, and the resulting interference patterns in accordance with the present invention. FIG. 7A is a schematic line drawing depicting a system 700 for creating complex 3D node patterns, the system 700 comprising a configuration of two ultrasonic transducers 106 that produce standing waves 706 in a growth medium 704 in a chamber 702. By orienting the transducers 106 orthogonal to each other, the standing waves 706 can be made to interfere with each other to produce patterns useful for constructing biomaterials and tissues. FIG. 7B depicts square channels generated from two simple sine waves and the intersection of the nodal planes and is a model-generated image of how the interference patterns from two simple sine waves transmitted from the transducers 106 interfere to produce a square lattice of nodal planes (dark lines). Growth of cells into tissue walls along this nodal lattice could produce square channels running through the microstructure. FIG. 7C depicts a lattice of complexly shaped channels and planes (dark lines) generated by using multiple harmonic frequencies from each transducer. This lattice was created using only the fundamental frequency and first three harmonics and comprises parallel channels of different shapes and sizes. An even more complex nodal microstructure may be created by adding a third transducer orthogonal to the first two. Harmonic frequencies added to the ultrasonic waves could produce an enormous variety of complex nodal lattices. Thus, by modulating the amplitudes of the harmonic frequencies, almost an infinite variety of tissue microstructures could be generated with the ultrasonic interference patterns. For example, such a microstructure may comprise sac-like structures interlaced with channels, much like alveoli and bronchioles in the lungs.

Figure 8A:
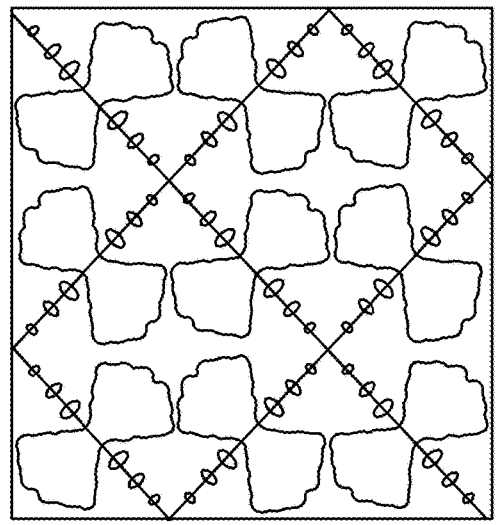
FIGS. 8A-8C depicts an embodiment of the generation of other types of complex node patterns (black lines) using two transducers and various combinations of harmonic frequencies in accordance with the present invention.
Figure 8B:
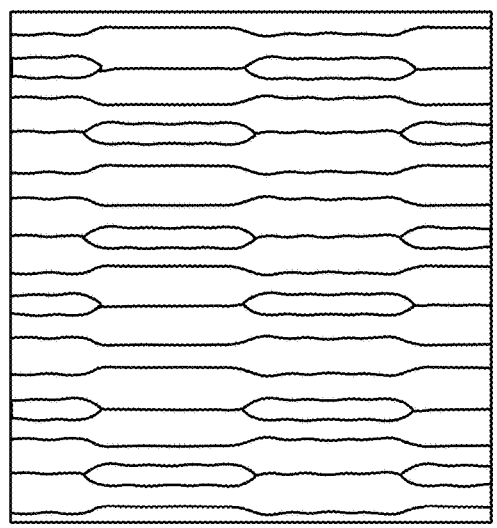
Figure 8C:
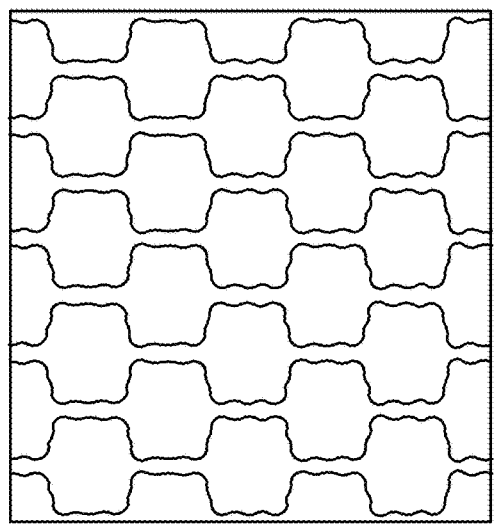

FIGS. 8A-8C depicts embodiments of other types of complex node patterns (black lines) generated using two transducers and various combinations of harmonic frequencies in accordance with the present invention. In some embodiments, an actual tissue microstructure from the body could be analyzed using 3D Fourier analysis to obtain the spatial frequencies of the structure. The amplitudes of these spatial frequencies would then be used to tune the combinations of harmonic frequencies used to generate the ultrasonic interference patterns. The method employs a holographic approach to tissue engineering by using the principle of interfering wave fields to produce realistic patterns in space.

Figure 9A:
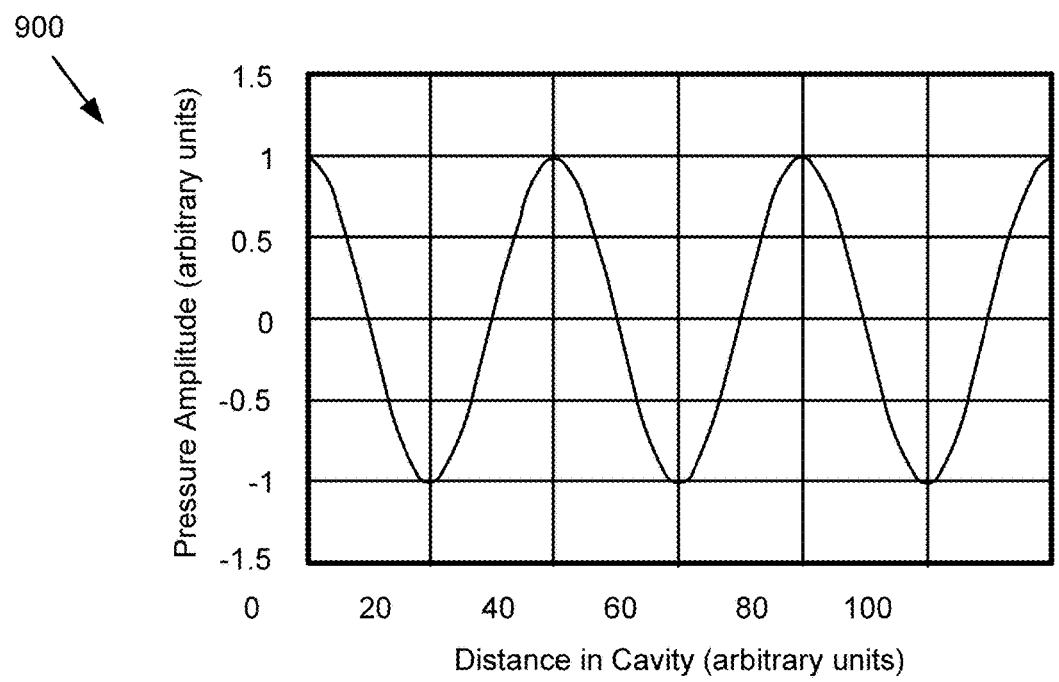
FIGS. 9A-9B depicts an embodiment of 9A a one-dimensional simple, single-frequency wavefield, and 9B a two-dimensional view of a three-dimensional tissue structure engineered from the superposition of three simple standing wavefields as shown in 9A in accordance with the present invention.
Figure 9B:
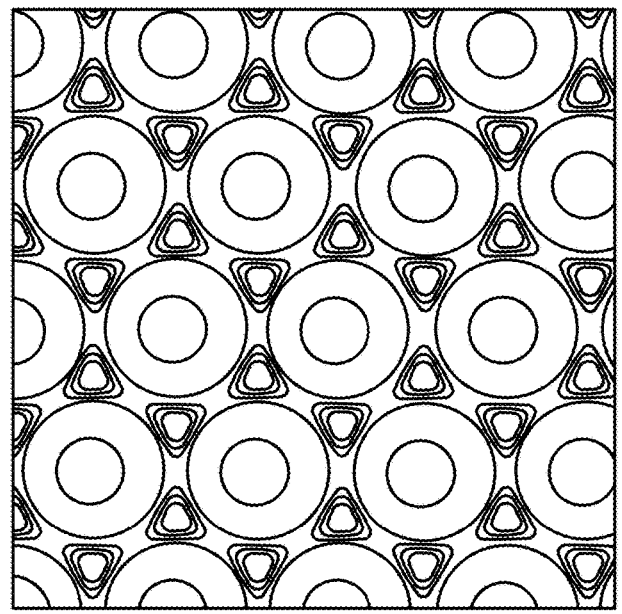

FIGS. 9A-9B depict an example 900 of a one-dimensional simple, single-frequency wavefield 9A, and a two-dimensional view of a three-dimensional tissue structure 9B engineered from the superposition of three simple standing wavefields as shown in 9A. The light and dark areas are antinodal regions which form continuous channels running through the structure, into and out of the drawing as portrayed. The nebulous and gradually varying amplitude variations would make it difficult to predict or control the growth of tissue structures of specific sizes, shapes, and configurations.

Figure 10A:
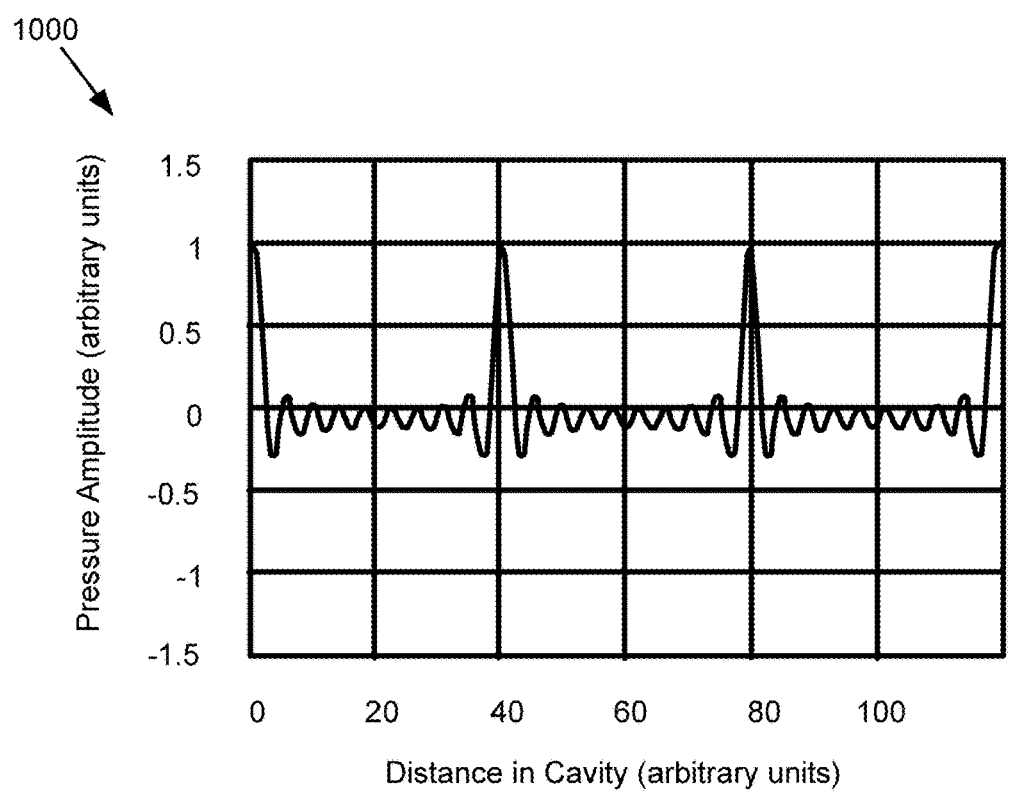
FIGS. 10A-10B depicts an embodiment of 10A one-dimensional complex, harmonic-modulated standing wavefield designed to produce pressure amplitude spikes and 10B a two-dimensional view of a three-dimensional tissue structure engineered from the superposition of three complex standing wavefields as shown in 10A in accordance with the present invention.
Figure 10B:
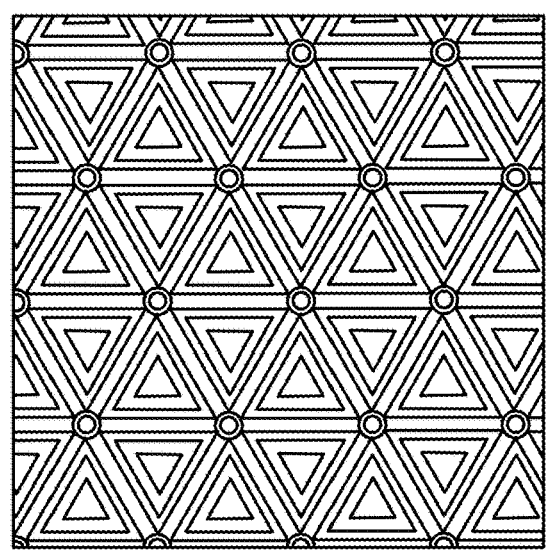

FIGS. 10A-10B illustrate embodiments 1000 of a complex standing waveform constructed from a specific superposition of harmonic frequencies to form sharp, distinctive pressure amplitude spikes 10A, and the formation of a triangular lattice of channels in a three-dimensional tissue structure 10B by the superposition of three planar complex standing waves as shown in 10A and confined in a cavity with a hexagonal cross-section in accordance with the present invention. In 10B, only the light regions that form the sharply defined triangular lattice are the antinodal regions which form continuous channels running through the structure, both into and out of the drawing as portrayed and across the microstructure as a triangular lattice. These antinodes correspond to the amplitude spikes in 10A. The triangular dark areas between the light-shaded lines are nodal regions, and correspond to the regions of the waveform with low pressure amplitudes ($\leq 0.2$). Tissue structures such as regular cell clusters (lobules) could form in these nodal regions.

Thus, in certain embodiments, complex, harmonic-modulated standing wavefield produces sharp, well-defined channels in the tissue structure that more closely resemble the structure of arteriole, capillary, and other ductal structures in tissue. The segmentation of cells into regular triangular, rectangular, or hexagonal cell clusters could also more closely resemble many tissue microstructures in the body, such as the lobules of the liver. Other organ tissues could be engineered from such geometrically regular structural units, such as the alveoli and bronchioles of the lung as shown in FIG. 11.

Figure 11:
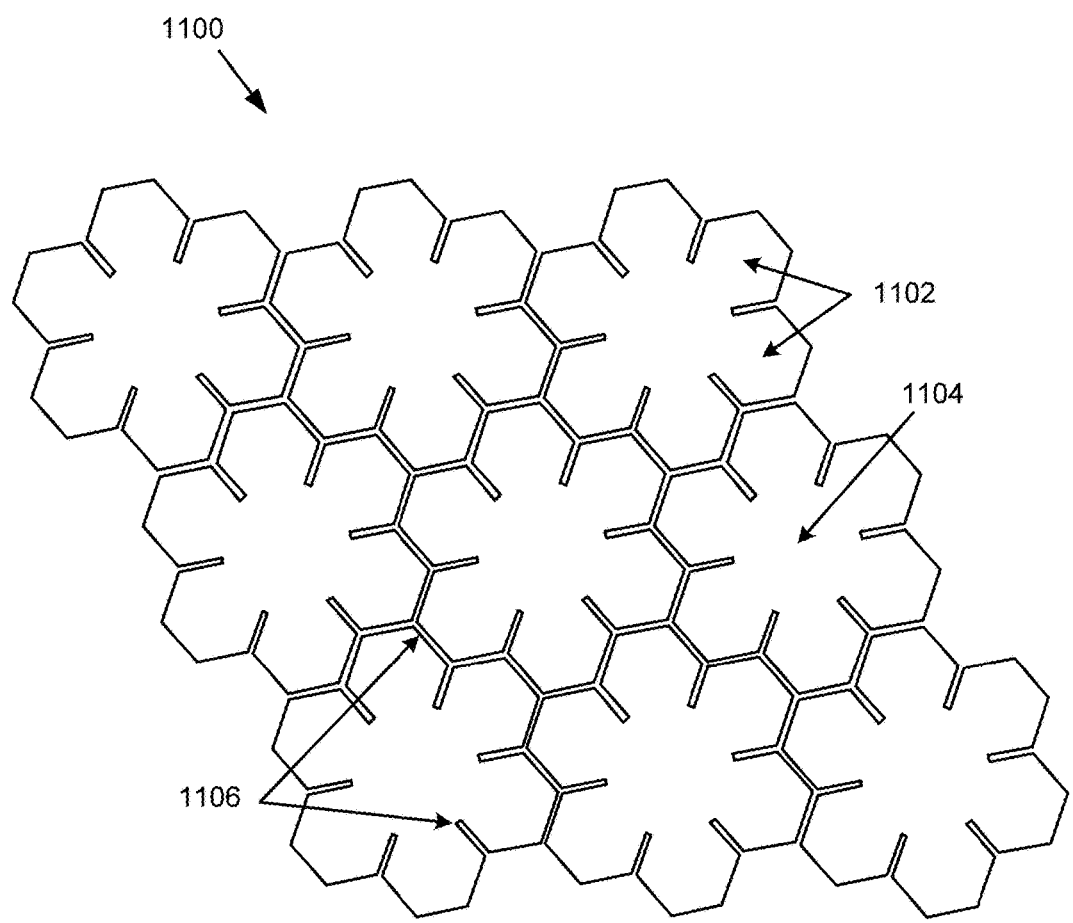
FIG. 11 is a schematic line drawing of an embodiment of an engineered tissue structure for replicating the alveolar and bronchiole structures of the lung using harmonic-modulated acoustic standing wavefields in accordance with the present invention.
Figure 12A:
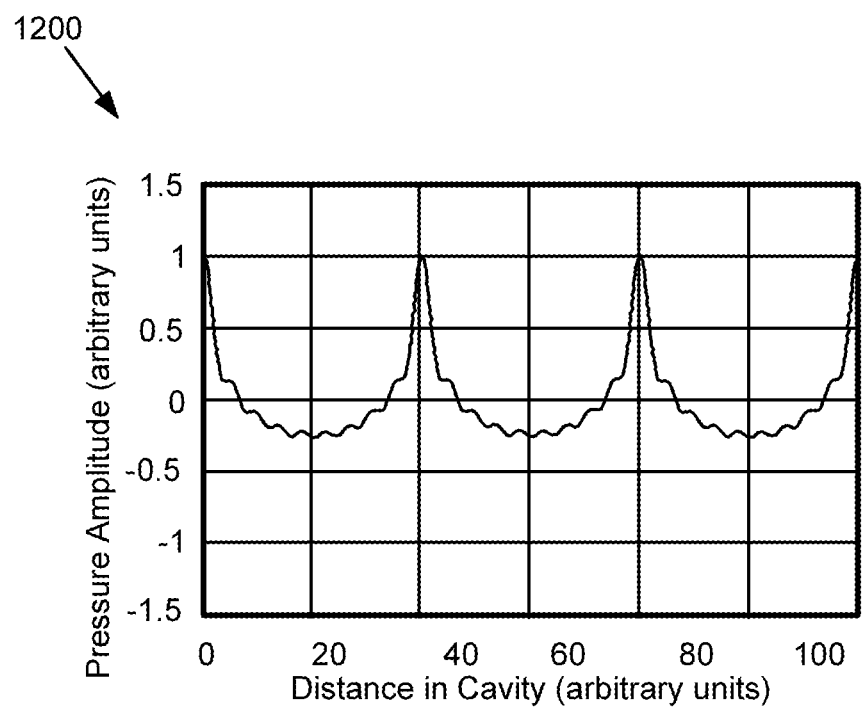
FIGS. 12A-12D depicts a an embodiment of complex, harmonic-modulated standing wavefields designed to produce amplitude spikes in accordance with the present invention.
Figure 12B:
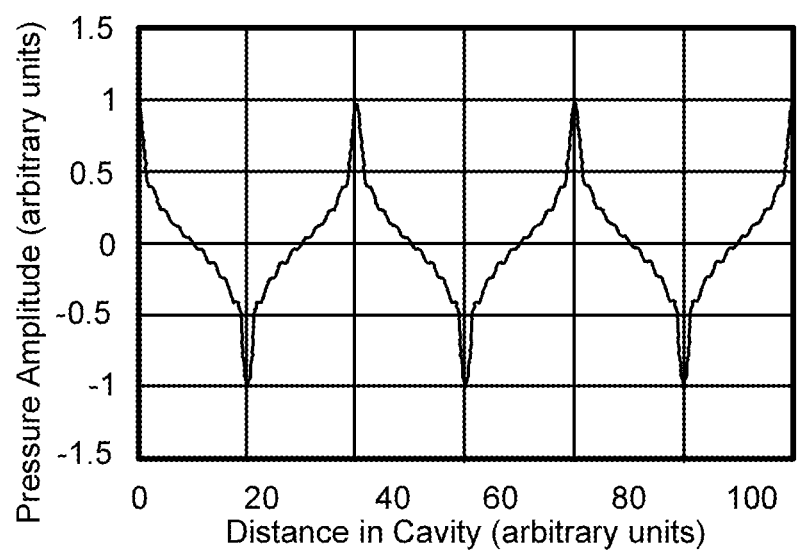
Figure 12C:
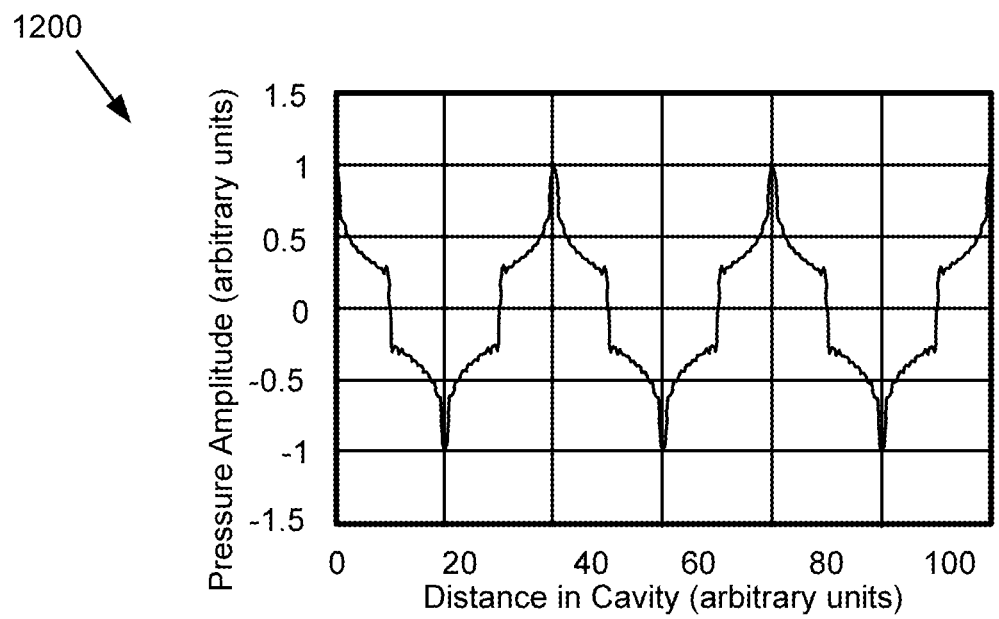
Figure 12D:
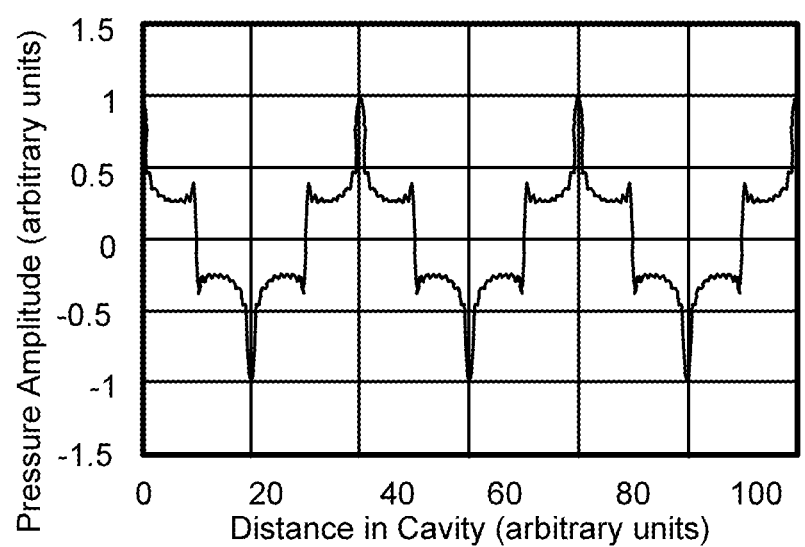

FIG. 11 is a schematic line drawing of an embodiment of an engineered tissue structure 1100 for replicating the alveolar 1102 and bronchiole 1104 structures of the lung using harmonic-modulated acoustic standing wavefields in accordance with the present invention. Such regular geometric structures could be produced in a manner similar to that shown in FIG. 10, except the interior of the hexagonal regions may be the empty alveolar 1102 and bronchiole 1104 cavities, and could therefore be generated from antinodal regions in the standing wavefield. The thin regions surrounding the alveoli may be the epithelial, elastin, and capillary walls 1106 of the alveoli 1102 and bronchioles 1104, and could be generated by a large part from nodal regions in the standing wavefield.

FIGS. 12A-12D depict embodiments of a complex, harmonic-modulated standing wavefields 1200 designed to produce highly localized amplitude spikes 1202 in accordance with the present invention. In some embodiments the wavefields 1200 comprise acoustic waves in fluids. The wavefields 1200 sometimes comprise stress-strain fields corresponding to acoustic waves in solids, electromagnetic fields, particle density fields (e.g., ions or electrons in a plasma, metal, or ionic conductor), and the like.

Such spikes 1202 may be useful in tissue engineering for patterning channels and cavities in tissue constructs. In certain embodiments they could also be used for a variety of other applications such as enhancing acoustic cavitation and sonoluminescence, improving stability and fusion yields in plasmas by producing an electromagnetic pinch or containment effect, inducing high-field effects in laser cavities, or enhancing electro-acoustic and acousto-ionic effects in liquid and solid electrolytes.

Figure 13:
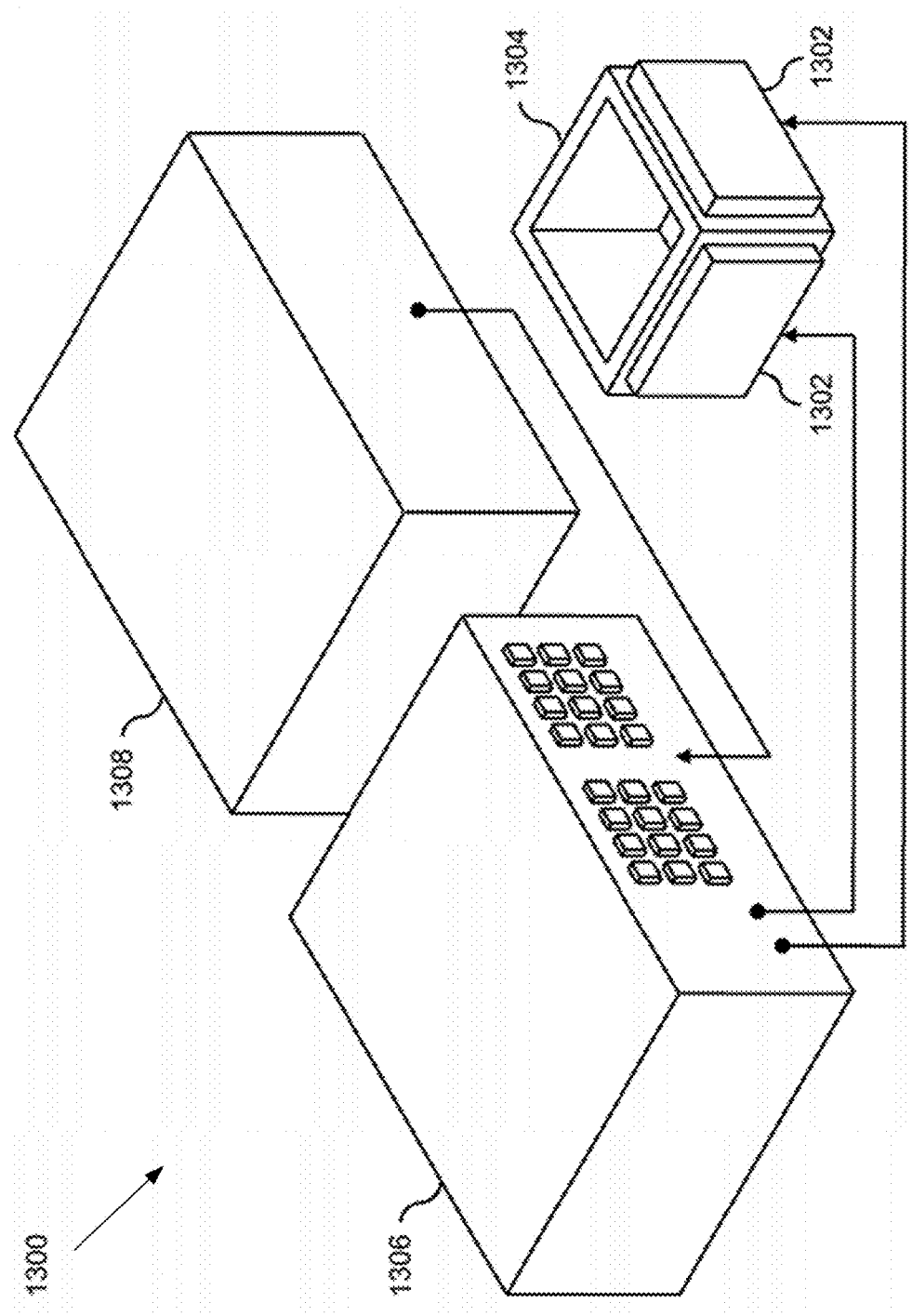
FIG. 13 depicts an embodiment of a system for spatial focusing and patterning using harmonic modulation of standing wavefields in accordance with the present invention.

FIG. 13 depicts an embodiment of a system 1300 for spatial focusing and patterning using harmonic modulation of standing wavefields in accordance with the present invention. As illustrated the embodiment comprises a wave transmitter 1302 that transmits waves at multiple frequencies; a chamber or cavity 1304 configured to generate standing waves; a control module 1306 to modulate the amplitudes of the individual harmonics in order to generate a desired wavefield pattern and an analysis module 1308 to calculate the amplitudes of individual harmonics corresponding to a desired wavefield pattern, material structure, or material configuration. In some embodiments the wave transmitter 1302 comprises an acoustic transducer, electromagnetic antenna, or laser. The multiple frequencies transmitted may comprise specifically a fundamental (lowest) frequency mode and harmonics of the fundamental frequency. In certain embodiments the wave transmitter 1302 comprises multiple wavefield sources to further focus the wavefield structure into a complex or well-defined pattern in one, two, or three dimensions. The standing waves may be planar, cylindrical, spherical, or one of the many other geometries that produce wave functions conducive to standing waves, such as spheroidal.

Various embodiments of the technology herein use the principle of Fourier's Theorem to focus the nodal or antinodal regions in a standing wave, or to generate more complex node-antinode patterns in the standing wave. Fourier's Theorem states that it is possible to construct any complex periodic vibration into a harmonic array of component frequencies. Fourier's Theorem may therefore be used to construct periodic waves more complex than a single-frequency wave, and that can therefore more sharply focus the acoustic pressure or electromagnetic fields at the nodal or antinodal regions.

In some embodiments a multifrequency, single transmitting source spatially focuses the wavefields. Such a system may generate a wide range of arbitrary complex wavefield patterns, eliminating the need for a transmitter with a special shaped design or face for focusing waves. Likewise this spatial focusing of the wavefields using multiple frequencies ("frequency focusing"), is not reliant on physical focusing elements such as lenses or mirrors.

In various embodiments the generation of highly defined nodal regions may increase the stability of levitated suspensions by confining particle motion to a greater extent. The generation of more highly defined antinodal regions—spikes—which may increase the localization of wavefield intensity for the generation of high intensity phenomena such as cavitation in fluids, thermal ablation, sonochemistry, or stimulation of neurons in biological organisms.

In certain embodiments wavefields of multiple frequencies and from multiple sources 1302 are used to create standing waves in a three-dimensional particle suspension. Particles may be attracted to and held at the nodal regions of the standing waves. The use of multiple frequencies and sources 1302 allows the creation of sharply defined and complexly structured nodal regions. The sharp definition of the nodal regions may additionally stabilize the particle structure by suppressing particle motion and oscillations within the nodal regions.

Thus, in some embodiments acoustic wavefields having multiple frequencies and multiple sources are used to create standing waves that function as a virtual template for holding particles in complex, highly stable, and highly resolved patterns. Computational modeling of the wavefields is sometimes used to select a set of frequencies and source locations to produce the particle structures. In some embodiments each acoustic source has the capability of generating acoustic waves comprised of a plurality of distinct frequencies. These distinct-frequency acoustic waves may form standing waves that superimpose (sum), creating complex standing wave structures with stable, highly defined nodal surfaces. They may also generate complex combinations of nodal surfaces forming "double-wall" and "triple-wall" features. The technology herein may further use a plurality of these multifrequency sources to generate complex geometric configurations of nodal surfaces. These configurations can then be used as virtual or acoustic-force templates for the patterning of particles in suspensions.

Figure 14:
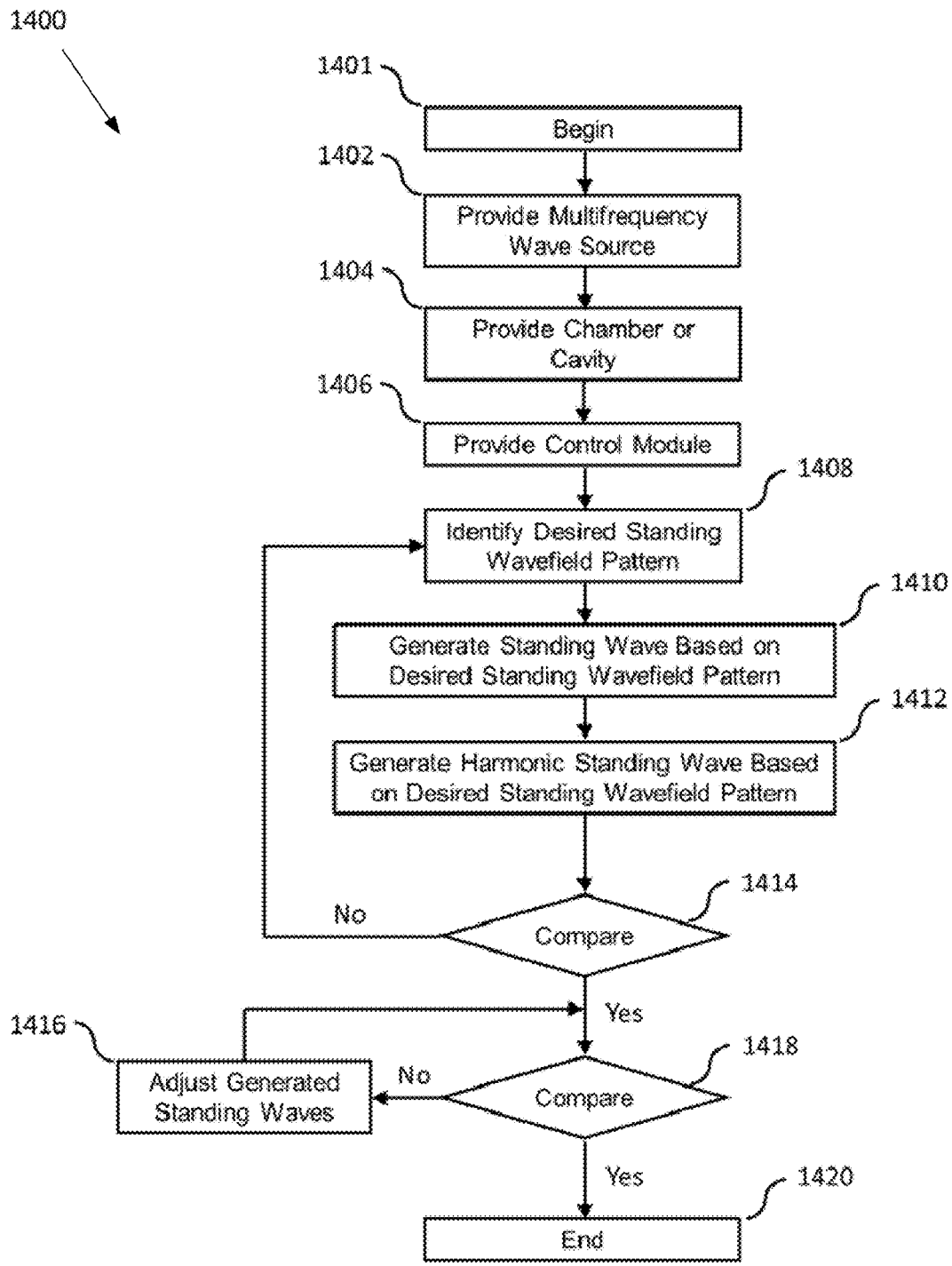
FIG. 14 depicts an embodiment of a method for spatial focusing and patterning using harmonic modulation of standing wavefields in accordance with the present invention.

FIG. 14 depicts a method 1400 for spatial focusing and patterning using harmonic modulation of standing wavefields in accordance with the present invention and comprising the steps: begin 1401, provide 1402 at least one wave transmitter, provide 1404 at least one chamber or cavity, provide 1406 at least one controller, identify 1408 at least one desired wave pattern, generate 1410 at least one standing wave according to the desired wave pattern, generate 1412 at least one additional standing wave according to the desired wave pattern, compare 1414 the resulting combined wave to the desired wave pattern, if the resulting combined wave pattern does not closely approximate the desired wave pattern then return to step 1410, if the resulting combined wave closely approximates the desired wave pattern then fine tune 1416 the resulting combined wave to generate a fine tuned wave pattern more closely approximating the desired wave pattern, compare 1418 the fine tuned wave pattern to the desired wave pattern, if the fine tuned wave pattern does not sufficiently approximate the desired wave pattern then return to step 1416, and if the fine tuned wave pattern sufficiently approximates the desired wave pattern then end 1420.

In certain embodiments the wave generated is an electromagnetic wave. The wave generated is sometimes an acoustical wave. In some embodiments the method spatially focuses and patterns the nodal and antinodal regions in standing wavefields by modulating the wavefields with harmonics (waves of higher frequency where the frequency is an integer value of the lowest or fundamental frequency).

Various embodiments include, but are not limited to, the generation of highly stable nodal regions for acoustic, electromagnetic, or optical levitation and manipulation of particulate matter in suspension, including biological cells, colloids, aerosols, and powders. Some embodiments generate complexly structured nodal regions for patterning biological materials in tissue engineering applications or nonbiological materials in fabrication applications. The method provided may generate antinodal regions with highly-localized, high acoustic pressures for enhanced cavitation, sonoluminescence, or sonochemistry in fluids. The method sometimes generates antinodal regions with highly-localized, high acoustic pressures to create well-defined channels or cavities in biological or nonbiological materials. In certain embodiments the method generates antinodal regions with highly-localized, high electromagnetic field strengths for initiating novel physical, chemical, or biological processes.

Figure 15:
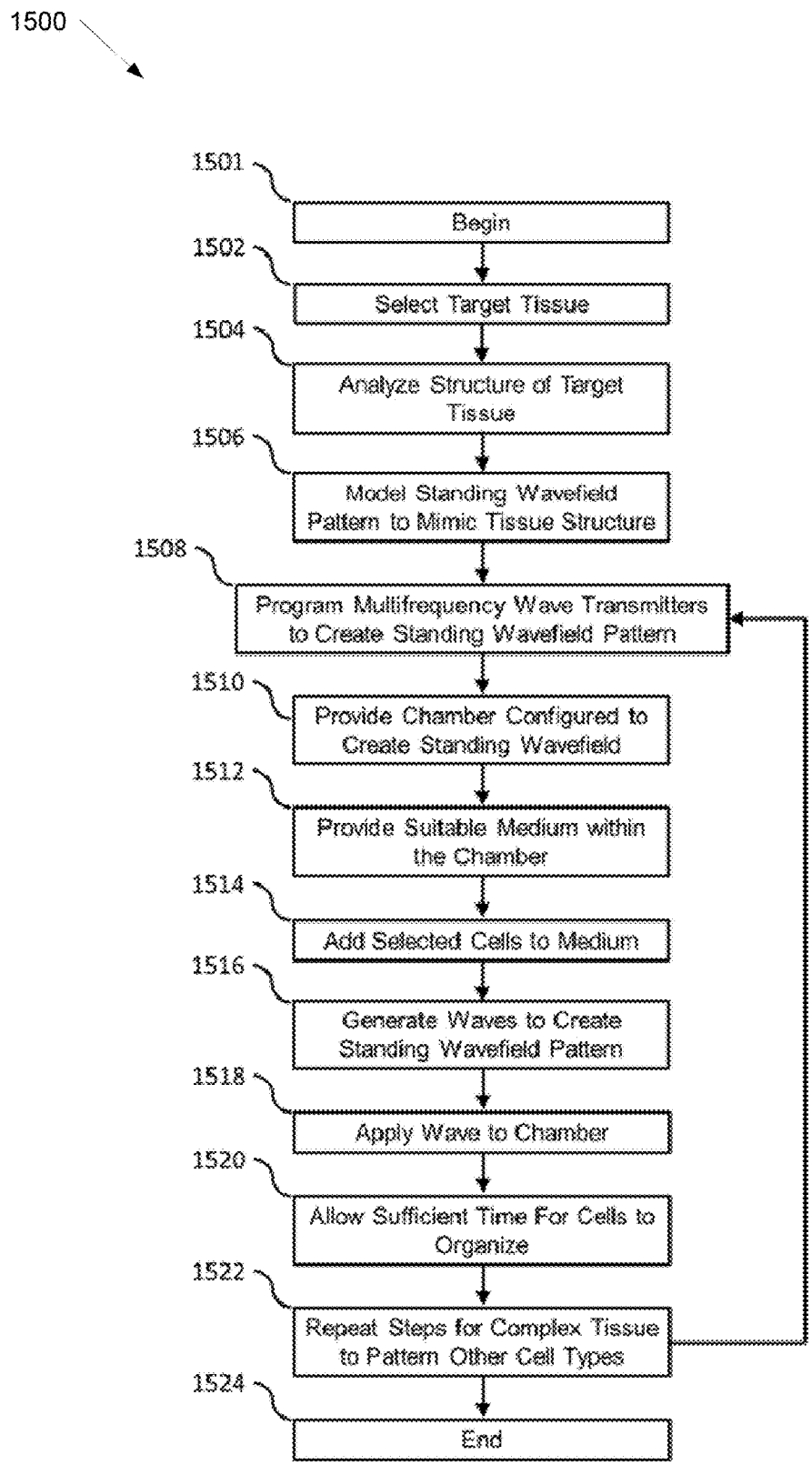
FIG. 15 depicts an embodiment of a method for cellular or tissue modeling using harmonic modulation of standing wavefields for spatial focusing and patterning in accordance with the present invention.

FIG. 15 depicts a method 1500 for cellular or tissue modeling using harmonic modulation of standing wavefields for spatial focusing and patterning and comprising the steps: select 1502 a target tissue, analyze 1504 the structure of the target tissue, model 1506 a standing wavefield that mimics the structure of the target tissue, program 1508 one or more multifrequency wave transmitters to create the specified standing wavefield, provide 1510 a chamber configured to create standing waves, provide 1512 a suitable medium within the chamber, add 1514 the selected cells to the medium, apply 1516 the wavefield to the chamber, allow 1518 sufficient time for the cells to organize into the form dictated by the standing wavefield and repeating 1520 the steps for complex tissues to pattern other cell types.

Embodiments of this technology include, but are not limited to, the patterning of cells into realistic tissue structures for tissue engineering; the patterning, consolidation, and bonding of particles for the fabrication of parts and devices having complex shapes; the stabilization of cell or particle layers in acoustic standing wave chambers or channels for nondestructive testing via ultrasonic, optical, or other noninvasive means; the refined separation of cells or particles for medical, chemical, or industrial processes; and microfluidic control of cells or particles without the need for conventional microfluidic devices with fixed channels and chambers.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for cellular or tissue modeling using harmonic modulation of standing wavefields for spatial focusing and patterning, the method comprising:
   a. selecting a target tissue;
   b. analyzing the structure of the target tissue;
   c. modeling a standing wavefield pattern that mimics that structure of the target tissue;
   d. programming a plurality of multifrequency wave transmitters to generate the waves necessary to create the standing wavefield pattern;
   e. providing a chamber configured to create a standing wavefield;
   f. providing a suitable medium within the chamber;
   g. adding selected cells to the medium;
   h. generating the waves necessary to create the standing wavefield pattern;
   i. applying the waves to the chamber; and
   j. allowing sufficient time for the cells to organize into the form dictated by the standing wavefield,
wherein the plurality of multifrequency wave sources are positioned at least one of 90°, and 120° relative to each other in order to create templates for a periodic three-dimensional channel with at least one of square, rectangular, triangular, and rhombohedral symmetry.

2. The method of claim 1 further comprising repeating the steps with a different cell type for a complex tissue.

3. The method of claim 2 further comprising generating a standing wave comprising an amplitude spike corresponding to an antinodal region in which a tissue structure with at least one of a continuous channel and a cavity could form, and nodal regions in which a tissue structure of at least one of regular cell clusters and sheets could form.

4. The method of claim 1 further wherein the chamber comprises at least one of cylindrical, conical, cubic, spherical, spheroid, rhombohedral, polyhedral, prismatic, and other geometry.

5. The method of claim 1 further comprising generating an acoustic standing wavefield as a force field to confine the cells or particles to as virtual channel and/or chamber through which they flow.

6. A method for cellular or tissue modeling using harmonic modulation of standing wavefields for spatial focusing and patterning, the method comprising:
   selecting a target tissue;
   analyzing the structure of the target tissue;
   modeling a standing wavefield pattern that mimics that structure of the target tissue;
   programming a plurality of multifrequency wave transmitters to generate the waves necessary to create the standing wavefield pattern;
   providing a chamber configured to create a standing wavefield;
   providing a suitable medium within the chamber;
   adding selected cells to the medium;
   generating the waves necessary to create the standing wavefield pattern;
   applying the waves to the chamber;
   allowing sufficient time for the cells to organize into the form dictated by the standing wavefield; and
   providing a plurality of acoustic sources with five-fold) (108°), seven-fold (128.57°), and eight-fold (135°) symmetry creating standing waves as templates for an aperiodic and random cell structure resembling tissue microstructure and/or disordered or a quasi-crystalline pattern in an atomic structure.

7. The method of claim 6, further comprising repeating the steps with a different cell type for a complex tissue.

8. The method of claim 7, further comprising generating a standing wave comprising an amplitude spike corresponding to
   an antinodal region in which a tissue structure with at least one of a continuous channel and a cavity could form,
   and nodal regions in which a tissue structure of at least one of regular cell clusters and sheets could form.

9. The method of claim 6, wherein the chamber comprises at least one of cylindrical, conical, cubic, spherical, spheroid, rhombohedral, polyhedral, prismatic, and other geometry.

10. The method of claim 6, further comprising generating an acoustic standing wavefield as a force field to confine the cells or particles to as virtual channel and/or chamber through which they flow.

11. A method for cellular or tissue modeling using harmonic modulation of standing wavefields for spatial focusing and patterning, the method comprising:
    selecting a target tissue;
    analyzing the structure of the target tissue;
    modeling a standing wavefield pattern that mimics that structure of the target tissue;
    programming a plurality of multifrequency wave transmitters to generate the waves necessary to create the standing wavefield pattern;
    providing a chamber configured to create a standing wavefield;
    providing a suitable medium within the chamber;
    adding selected cells to the medium;
    generating the waves necessary to create the standing wavefield pattern;
    applying the waves to the chamber;
    allowing sufficient time for the cells to organize into the form dictated by
    the standing wavefield; and
analyzing, with 3D Fourier analysis, a 3D microstructure of the target tissue obtained by at least one of microtoming and imaging successive slices of a tissue sample, and 3D microscopic computed tomography (micro-CT).

12. The method of claim 11, further comprising repeating the steps with a different cell type for a complex tissue.

13. The method of claim 12, further comprising generating a standing wave comprising an amplitude spike corresponding to
    an antinodal region in which a tissue structure with at least one of a continuous channel and a cavity could form,
    and nodal regions in which a tissue structure of at least one of regular cell clusters and sheets could form.

14. The method of claim 11, wherein the chamber comprises at least one of cylindrical, conical, cubic, spherical, spheroid, rhombohedral, polyhedral, prismatic, and other geometry.

15. The method of claim 11, further comprising generating an acoustic standing wavefield as a force field to confine the cells or particles to as virtual channel and/or chamber through which they flow.

* * * * *